(12) United States Patent
Takeshima et al.

(10) Patent No.: US 12,295,703 B2
(45) Date of Patent: May 13, 2025

(54) ULTRASOUND IMAGING APPARATUS

(71) Applicant: FUJIFILM Healthcare Corporation, Kashiwa (JP)

(72) Inventors: Hirozumi Takeshima, Chiba (JP); Tomohiko Tanaka, Chiba (JP); Misaki Maruyama, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 71 days.

(21) Appl. No.: 18/216,058

(22) Filed: Jun. 29, 2023

(65) Prior Publication Data

US 2024/0000318 A1 Jan. 4, 2024

(30) Foreign Application Priority Data

Jul. 4, 2022 (JP) .................................. 2022-107739

(51) Int. Cl.
*A61B 5/00* (2006.01)
(52) U.S. Cl.
CPC .................................. *A61B 5/0095* (2013.01)
(58) Field of Classification Search
CPC .................................................. A61B 5/0095
See application file for complete search history.

(56) References Cited

U.S. PATENT DOCUMENTS

| 2012/0323122 A1* | 12/2012 | Okubo | ................. | A61B 8/4488 |
| | | | | 600/443 |
| 2014/0118749 A1* | 5/2014 | Nakajima | .......... | G01N 29/2418 |
| | | | | 356/519 |
| 2015/0335252 A1* | 11/2015 | Hirota | ................. | A61B 5/7246 |
| | | | | 600/407 |

FOREIGN PATENT DOCUMENTS

| JP | 6317847 B | 4/2018 |
| JP | 2019-213680 A | 12/2019 |

* cited by examiner

*Primary Examiner* — Joel F Brutus
(74) *Attorney, Agent, or Firm* — Paul Teng

(57) ABSTRACT

A laser beam is applied to a photoacoustic wave generation source multiple times in a reception period of ultrasound waves during photoacoustic imaging. As a result, a plurality of photoacoustic waves are generated from the photoacoustic wave generation source in the reception period and received by a reception unit of an ultrasound imaging apparatus. The positions of the plurality of photoacoustic waves on a time axis is adjusted, and the plurality of photoacoustic waves are averaged. A photoacoustic image is generated based on a signal obtained through the averaging.

8 Claims, 8 Drawing Sheets

ULTRASOUND IMAGING APPARATUS

CROSS REFERENCE TO RELATED APPLICATION

This application claims priority to Japanese Patent Application No. 2022-107739 filed on Jul. 4, 2022, which is incorporated herein by reference in its entirety including the specification, claims, drawings, and abstract.

TECHNICAL FIELD

The present disclosure relates to an ultrasound imaging apparatus and, in particular, relates to a technique of generating images by receiving ultrasound waves from an ultrasound generation source that is inserted within a subject.

BACKGROUND

Catheter therapy is a surgical method that typically imposes less burden on patients than does thoracotomy or other surgical procedures. As such, catheter therapy is mainly used to cure diseases including narrowing of the blood vessels. Monitoring a positional relationship between a region to be treated and a catheter is the key to catheter therapy. X-ray fluoroscopy may be used as an imaging method for assistance in monitoring this positional relationship. Also, there is known a technique of using an ultrasound image as an assistance image as disclosed in JP 2019-213680 A.

JP 2019-213680 A discloses an apparatus that generates ultrasound images by receiving ultrasound waves from an ultrasound generation source that is incorporated in a guide wire. Specifically, the tip position of the guide wire is estimated using an image of the ultrasound generation source that is dependent on time difference of arrival; that is, the difference between the time instants when ultrasound waves (ultrasound waves emanating from the ultrasound generation source) reach a transducer array of an ultrasound probe, or a distance from an imaging region. JP 2019-213680 A also discloses a technique of monitoring a relative positional relationship between an imaged result and the tip of the guide wire using the estimated result.

JP 6317847 B discloses a technique of providing a light-absorbing member at the tip of an insert, wherein the light-absorbing member absorbs light emanating from a light guide member to generate photoacoustic waves, and in response to reception of the photoacoustic waves, the tip of the insert is visualized. JP 6317847 B also discloses a technique of generating one image by averaging detection signals of photoacoustic waves that are generated from the light-absorbing member when pulsed light is applied to the light-absorbing member multiple times and that are received by an ultrasound probe multiple times.

As the intensity of photoacoustic waves is low, monitoring the tip position of the insert using photoacoustic waves may involve difficulty. To address this, the intensity may be increased by applying a plurality of pulsed light beams, receiving a plurality of photoacoustic waves, and summing the plurality of photoacoustic waves. However, as the cycle period of pulsed light is limited by an ultrasound propagation time that varies depending on the depth of a region of interest, a reception period for receiving a plurality of photoacoustic waves increases, thereby causing an issue in that the update speed of ultrasound images decreases.

The present disclosure is directed toward increasing the intensity of received photoacoustic waves without increasing the reception period of photoacoustic waves generated from a photoacoustic wave generation source.

SUMMARY

According to one aspect of the present disclosure, there is provided an ultrasound imaging apparatus comprising imaging means for transmitting and receiving ultrasound waves toward and from a subject, thereby generating an ultrasound image; photoacoustic imaging means for receiving photoacoustic waves generated from a photoacoustic wave generation source inserted within the subject, thereby imaging a position of the photoacoustic wave generation source; and control means for generating photoacoustic waves from the photoacoustic wave generation source with a cycle shorter than a reception period during which photoacoustic waves generated from the photoacoustic wave generation source are received, the reception period being determined based on a region that is to be imaged using photoacoustic waves.

The control means may generate photoacoustic waves from the photoacoustic wave generation source a number of times in the reception period, and the number of times may be determined based on a limit value for an intensity of light applied to the photoacoustic wave generation source for generating photoacoustic waves from the photoacoustic wave generation source.

The control means may change an intensity and a light emission period of light applied to the photoacoustic wave generation source for generating photoacoustic waves from the photoacoustic wave generation source depending on a count of light emissions of the light applied to the photoacoustic wave generation source for generating photoacoustic waves from the photoacoustic wave generation source and an interval between the light emissions.

The control means may generate photoacoustic waves from the photoacoustic wave generation source a number of times in the reception period, and the photoacoustic imaging means may image the position of the photoacoustic wave generation source based on a plurality of photoacoustic waves received in the reception period.

The photoacoustic imaging means may further remove an artifact that occurs in response to the plurality of photoacoustic waves.

The photoacoustic imaging means may apply phase alignment processing to the plurality of photoacoustic waves and may, for example, average the plurality of photoacoustic waves to which phase alignment has been applied, with the positions of the plurality of photoacoustic waves on a time axis being adjusted.

The photoacoustic imaging means may average the plurality of photoacoustic waves to which phase alignment has not been applied, with the positions of the plurality of photoacoustic waves on a time axis being adjusted.

The photoacoustic imaging means may estimate a photoacoustic wave to which phase alignment processing has not been applied, through reverse phase alignment processing from a result obtained after phase alignment processing has been applied.

The present disclosure enables increasing the intensity of received photoacoustic waves without increasing the reception period of photoacoustic waves generated from a photoacoustic wave generation source.

BRIEF DESCRIPTION OF DRAWINGS

Embodiments of the present disclosure will be described based on the following figures, wherein.

DESCRIPTION OF EMBODIMENTS

Figure 1:
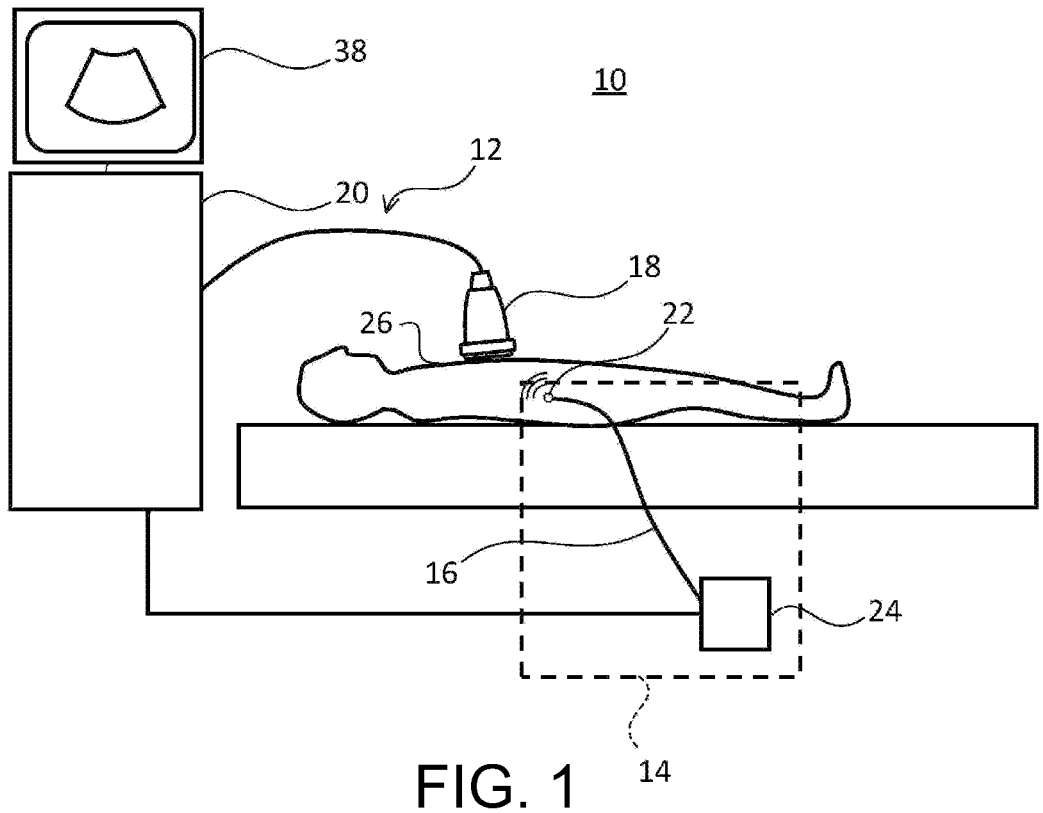
FIG. 1 is a block diagram illustrating a structure of a medical assistance system according to an embodiment of the present disclosure.

Referring to FIG. 1, a medical assistance system according to an embodiment of the present disclosure will be described below. FIG. 1 illustrates a structure of a medical assistance system according to an embodiment of the present disclosure. A medical assistance system 10 according to an embodiment of the present disclosure is, by way of example, a system that assists in performing therapy using a catheter. This example is a mere example, and therapy in which the medical assistance system 10 assists is not limited to therapy performed using a catheter but may include any therapy performed using an instrument inserted into a subject.

The medical assistance system 10 includes, by way of example, an ultrasound imaging apparatus 12, an ultrasound generator 14, and a living body inserter 16.

The ultrasound imaging apparatus 12, which includes an ultrasound probe 18 and a main unit 20, generates image data through transmission and reception of ultrasound waves using the ultrasound probe 18. For example, the ultrasound imaging apparatus 12 transmits ultrasound waves toward inside of a subject 26 and receives ultrasound waves reflected from inside the subject 26, thereby generating image data that represent tissue inside the subject 26. As will be described later, the ultrasound imaging apparatus 12 receives ultrasound waves generated from an ultrasound generation source 22, thereby generating image data.

The ultrasound generator 14, which includes the ultrasound generation source 22 and a driver 24, is a device that generates ultrasound waves. The ultrasound generator 14 is incorporated in the living body inserter 16.

The living body inserter 16 is an elongated tubular instrument, such as a balloon catheter, a microcatheter, a feeding catheter, or another therapeutic instrument, or a guide wire for guiding such a therapeutic instrument to the intended location. In the example below, the living body inserter 16 is, by way of example, a guide wire.

The ultrasound generation source 22 generates ultrasound waves, by way of example, through the photoacoustic effect. The ultrasound generation source 22 may generate ultrasound waves through principles other than the photoacoustic effect. For example, the ultrasound generation source 22 may be composed of an ultrasound transducer, such as a piezoelectric element. In this case, the driver 24 serves as a piezoelectric element driving circuit to generate ultrasound waves from the ultrasound generation source 22. In the example below, the ultrasound generation source 22 generates ultrasound waves through the photoacoustic effect. It should be noted that the ultrasound generation source 22 corresponds to an example of the photoacoustic wave generation source.

Figure 2:
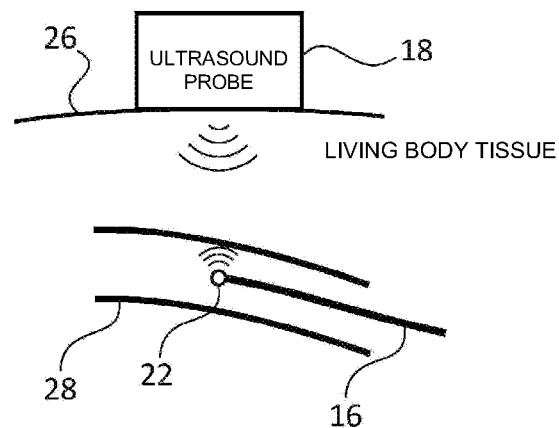
FIG. 2 illustrates a living body inserter inserted within a subject and an ultrasound generation source.

Referring to FIGS. 1 and 2, the ultrasound generator 14 will be described in detail below. FIG. 2 illustrates the living body inserter 16 inserted within the subject 26 and the ultrasound generation source 22.

The ultrasound generator 14 includes an optical fiber, which is not illustrated in the figures. The living body inserter 16 is, by way of example, a flexible hollow guide wire, and the optical fiber is provided along this living body inserter 16. The ultrasound generation source 22 is located at a first end of the optical fiber (the end that is inserted into the subject 26). The driver 24 is located at a second end of the optical fiber (the end that is opposite the end where the ultrasound generation source 22 is located). The driver 24 includes, by way of example, a light source that generates a laser beam. The optical fiber, which serves as a light guide member that guides light, guides the laser beam emitted from the driver 24 to the ultrasound generation source 22 located at the first end of the optical fiber. The ultrasound generator 14 and the living body inserter 16 in the form of a guide wire may constitute an apparatus that is sometimes referred to as a photoacoustic source-incorporating wire.

In the example illustrated in FIG. 2, the living body inserter 16 in the form of a guide wire is inserted into a blood vessel 28 that is present inside the subject 26. As the first end of the optical fiber is located at a first end of the living body inserter 16 (the end that is inserted into the subject 26), the ultrasound generation source 22 located at the first end of the optical fiber is located at the first end of the living body inserter 16. It should be noted that, although, in the example illustrated in FIG. 2, one ultrasound generation source 22 is provided at the first end of the living body inserter 16, the location where the ultrasound generation source 22 is placed is not limited to the first end of the living body inserter 16. In addition, a plurality of ultrasound generation sources 22 may be provided.

The ultrasound generation source 22 receives a laser beam emanating from the driver 24, thereby generating photoacoustic waves serving as ultrasound waves. For example, the ultrasound generation source 22 is composed of, for example, a known dye (for example, a photosensitizer), metal nanoparticles, or a carbon-based compound. The first end of the optical fiber and the ultrasound generation source 22 provided at this first end are covered with, for example, a sealing member that is made of resin.

Photoacoustic waves generated from the ultrasound generation source 22 are received by the ultrasound probe 18 that is placed on the body surface of the subject 26. Based on the photoacoustic waves received by the ultrasound probe 18, the main unit 20 generates image data that represent the ultrasound generation source 22. The ultrasound probe 18 transmits ultrasound waves toward the inside of the subject 26 and receives ultrasound waves reflected from inside the subject 26, and, based on these received ultrasound waves, the main unit 20 generates image data (for example, cross-sectional image data) that represent tissue inside the subject 26 (for example, tissue including the blood vessel 28). An image that represents the ultrasound generation source 22 is superimposed on a cross-sectional image that represents tissue inside the subject 26, and these images are displayed on a display. This enables the operator to monitor the position of the first end of the living body inserter 16 inside the subject 26 (for example, inside the blood vessel 28).

Figure 3:
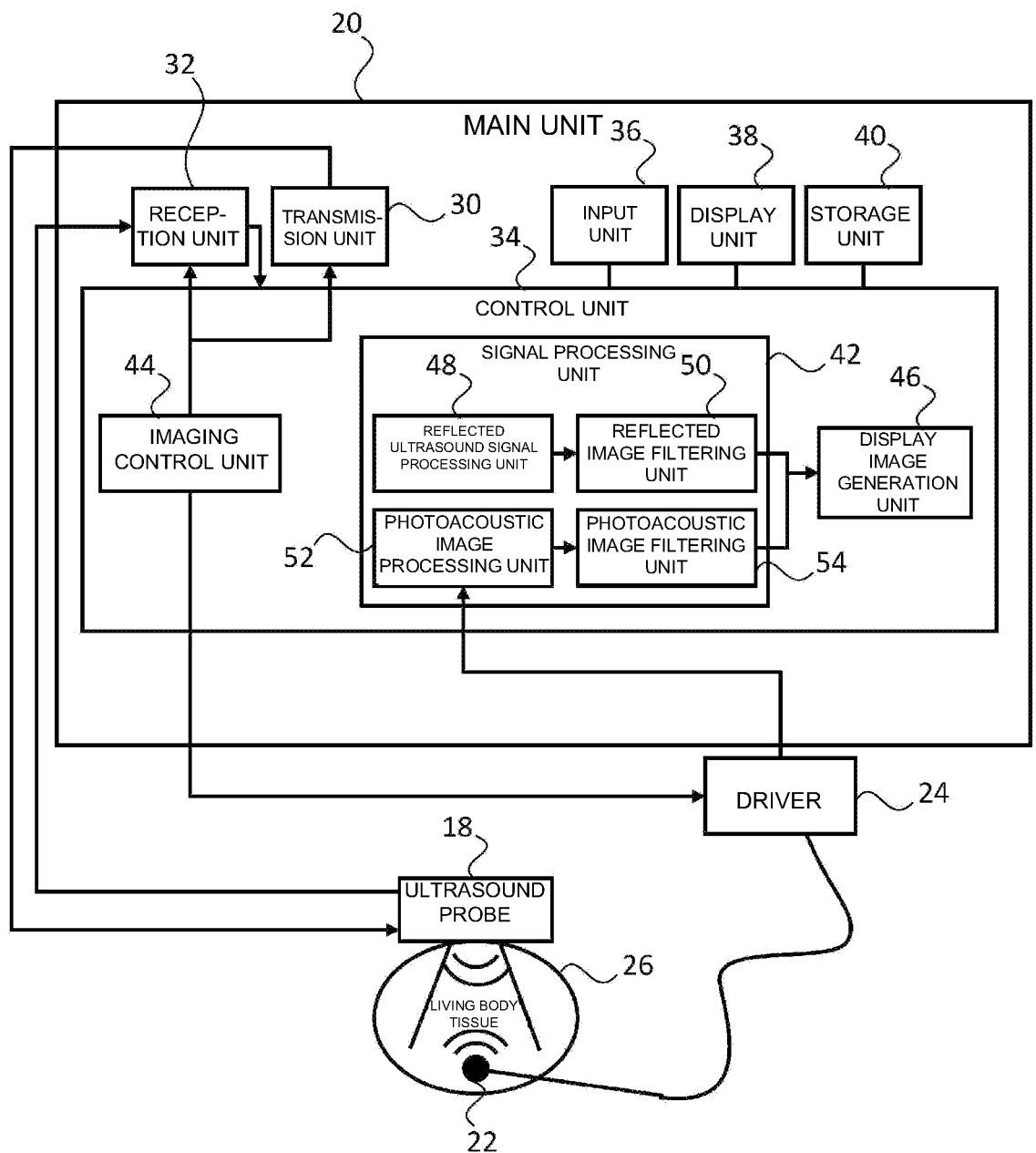
FIG. 3 is a block diagram illustrating a structure of an ultrasound imaging apparatus according to an embodiment of the present disclosure.

Referring to FIG. 3, a structure of the ultrasound imaging apparatus 12 will be described below. FIG. 3 is a block diagram illustrating a structure of the ultrasound imaging apparatus 12.

The ultrasound probe 18 is a device that transmits and receives ultrasound waves. The ultrasound probe 18 includes, for example, a 1D array transducer. The 1D array transducer is composed of a one-dimensional arrangement of a plurality of ultrasound transducers. The 1D array transducer forms an ultrasound beam, and the ultrasound beam is electronically scanned repeatedly. As a result, a scanning plane is formed inside the living body each time electronic scanning is performed. The scanning plane corresponds to a two-dimensional echo data capturing space. The ultrasound probe 18 may include a 2D array transducer including a plurality of transducer elements that are two-dimensionally arranged, rather than a 1D array transducer. The 2D array transducer forms an ultrasound beam, and the ultrasound beam is electronically scanned repeatedly, thereby forming a scanning plane as a two-dimensional echo data capturing space each time electronic scanning is performed. The ultrasound beam may be scanned two-dimensionally, thereby forming a three-dimensional space as a three-dimensional echo data capturing space. Examples of scanning methods that may be used include, for example, sector scanning, linear scanning, or convex scanning. Examples of ultrasound probes that may be used are not limited to an ultrasound probe placed on the body surface but include an ultrasound probe placed somewhere other than on the body surface, such as an ultrasound probe for use in, for example, intravascular ultrasound (IVUS).

The main unit 20 includes a transmission unit 30, a reception unit 32, a control unit 34, an input unit 36, a display unit 38, and a storage unit 40.

The transmission unit 30 serves as a transmission beam former. The reception unit 32 serves as a reception beam former. During transmission, the transmission unit 30 supplies a plurality of transmission signals having a certain delay relationship to a plurality of ultrasound transducers included in the ultrasound probe 18. As a result, a transmission beam of ultrasound is formed. During reception, reflected waves (RF signal) emanating from inside the living body are received by the ultrasound probe 18, thereby outputting a plurality of reception signals from the ultrasound probe 18 to the reception unit 32. The reception unit 32 applies phase alignment and summing processing to the plurality of reception signals, thereby forming a reception beam. This beam data are output to a signal processing unit 42 of the control unit 34. More specifically, the reception unit 32 applies delay processing to reception signals obtained from the respective ultrasound transducers in accordance with delay processing conditions applicable to the respective ultrasound transducers and applies summing processing to a plurality of reception signals obtained from a plurality of ultrasound transducers, thereby forming a reception beam. The delay processing conditions are defined by reception delay data that represent delay time. A reception delay data set (in other words, a set of delay time) corresponding to a plurality of ultrasound transducers is supplied from the control unit 34.

An ultrasound beam (in other words, the transmission beam or the reception beam) is electronically scanned by the action of the transmission unit 30 and the reception unit 32, thereby forming a scanning plane. The scanning plane corresponds to a plurality of items of beam data, which constitute reception frame data (specifically, RF signal frame data). It should be noted that each item of beam data is composed of a plurality of items of echo data that are successive in the depth direction. An ultrasound beam is electronically scanned repeatedly, so that a plurality of items of reception frame data that are successive on a time axis are output from the reception unit 32. These constitute a reception frame array.

Volume imaging may be performed using, for example, a 2D array transducer; in this case, in addition to the above-described processing, an ultrasound beam may be electronically scanned two-dimensionally by the action of the transmission unit 30 and the reception unit 32, thereby forming a three-dimensional echo data capturing space. Volume data serving as a set of echo data are obtained from this three-dimensional echo data capturing space. An ultrasound beam is electronically scanned repeatedly, so that a plurality of items of volume data that are successive on the time axis are output from the reception unit 32. These constitute a volume data array.

The control unit 34, which includes the signal processing unit 42, an imaging control unit 44, and a display image generation unit 46, controls transmission and reception of ultrasound performed by the ultrasound probe 18 to generate image data based on received ultrasound. The control unit 34 controls the ultrasound generator 14. Specifically, the control unit 34 controls emission of a laser beam performed by the driver 24 to generate image data based on ultrasound emanating from the ultrasound generation source 22.

The signal processing unit 42 is a device that applies signal processing including detection, log compression, and conversion functions, such as a coordinate conversion function and an interpolation processing function performed by a DSC (digital scan converter), to beam data output from the reception unit 32, thereby generating image data (for example, B-mode image).

The imaging control unit 44 controls timing of imaging of a reflected ultrasound image and timing of imaging of a photoacoustic image. The imaging control unit 44 also controls the number of times a reflected ultrasound image is imaged and the number of times a photoacoustic image is imaged.

The reflected ultrasound image is image data that are generated based on ultrasound transmitted from the ultrasound probe 18 and reflected inside the subject 26 (in other words, reflected waves). In other words, the reflected ultrasound image is image data that are generated based on a reflected ultrasound signal output from the reception unit 32 which has received reflected ultrasound waves. The imaging of the reflected ultrasound image comprises transmission of ultrasound waves from the ultrasound probe 18 and reception of the transmitted reflected waves of ultrasound, thereby generating a reflected ultrasound image. In the following description, the imaging of the reflected ultrasound image is referred to as "reflected ultrasound imaging".

The photoacoustic image is image data that are generated based on photoacoustic waves emanating from the ultrasound generation source 22. In other words, the photoacoustic image is image data that are generated based on a photoacoustic signal output from the reception unit 32 which has received photoacoustic waves. The imaging of the photoacoustic image comprises generation of the photoacoustic image based on photoacoustic waves emanating from the ultrasound generation source 22. In the following description, the imaging of the photoacoustic image is referred to as "photoacoustic imaging".

The imaging control unit 44 calculates an imaging count, an imaging cycle, and timing for each of the reflected ultrasound imaging and the photoacoustic imaging in accordance with conditions which will be described later. To perform the reflected ultrasound imaging based on the results of this calculation, the imaging control unit 44 controls transmission of ultrasound waves performed by the transmission unit 30 and reception of ultrasound waves performed by the reception unit 32. As a result, a reflected ultrasound signal is generated, and a reflected ultrasound image is generated based on this reflected ultrasound signal. To perform the photoacoustic imaging, the imaging control unit 44 controls emission of a laser beam performed by the driver 24 and reception of photoacoustic waves performed by the reception unit 32. As a result, a photoacoustic signal is generated, and a photoacoustic image is generated based on this photoacoustic signal. It should be noted that the imaging control unit 44 corresponds to an example of the control means.

The signal processing unit 42 includes a reflected ultrasound signal processing unit 48, a reflected image filtering unit 50, a photoacoustic image processing unit 52, and a photoacoustic image filtering unit 54.

The reflected ultrasound signal processing unit 48 applies signal processing to a reflected ultrasound signal (RF signal) output from the reception unit 32 in response to performance of the reflected ultrasound imaging, thereby generating a reflected ultrasound image, such as a B-mode image. In other words, the reflected ultrasound signal processing unit 48 images the reflected ultrasound signal, thereby generating a reflected ultrasound image. It should be noted that the transmission unit 30, the reception unit 32, and the reflected ultrasound signal processing unit 48 correspond to an example of the imaging means.

The reflected image filtering unit 50 applies filtering processing to the reflected ultrasound image output from the reflected ultrasound signal processing unit 48.

The photoacoustic image processing unit 52 applies signal processing to a photoacoustic signal output from the reception unit 32 in response to performance of the photoacoustic imaging, thereby generating a photoacoustic image. In other words, the photoacoustic image processing unit 52 images the photoacoustic signal, thereby generating a photoacoustic image. It should be noted that the transmission unit 30, the reception unit 32, and the photoacoustic image processing unit 52 correspond to an example of the photoacoustic imaging means.

The photoacoustic image filtering unit 54 applies filtering processing to the photoacoustic image output from the photoacoustic image processing unit 52.

Based on an image generated by the signal processing unit 42, the display image generation unit 46 generates a display image that is displayed on the display unit 38. For example, the display image generation unit 46 superimposes a photoacoustic image on a reflected ultrasound image, thereby generating a display image. The display image generation unit 46 causes the display image to be displayed on the display unit 38.

It should be noted that, other than the imaging control unit 44, the photoacoustic image processing unit 52, and the photoacoustic image filtering unit 54, the structure may be the same as the structure of a known ultrasound imaging apparatus.

The input unit 36 is a device through which the user inputs, for example, imaging requirements or instructions to the main unit 20. For example, the input unit 36 may include an operation panel, switches, buttons, a keyboard, a mouse, or a joystick.

The display unit 38 is a display, such as a liquid crystal display or an EL display. A reflected ultrasound image or a photoacoustic image is displayed on the display unit 38. A reflected ultrasound image and a photoacoustic image may be displayed on the display unit 38 with the photoacoustic image being superimposed on the reflected ultrasound image. The display unit 38 may be an apparatus that serves as both a display and the input unit 36. For example, a GUI (Graphic User Interface) may be implemented by the display unit 38. A touch panel or another user interface may be implemented by the display unit 38.

The storage unit 40 is a device that constitutes one or a plurality of storage areas for storing data. The storage unit 40 may include, for example, a hard disk drive (HDD), a solid-state drive (SSD), various types of memory (such as RAM, DRAM, or ROM), other storage devices (such as an optical disk), or a combination thereof. For example, a reflected ultrasound image or a photoacoustic image is stored in the storage unit 40.

The control unit 34 can be implemented through the use of hardware resources such as a processor or an electronic circuit, and this implementation may comprise optionally using memory or other devices. The control unit 34 may also be implemented by, for example, a computer. In other words, the control unit 34 may be implemented, either entirely or in part, through the cooperation of hardware resources such as a CPU (Central Processing Unit) or memory included in a computer, and software (program) that defines the operation of the CPU or the like. Such programs are stored in the storage unit 40 or another storage device through a storage medium such as a CD or a DVD, or over a communication channel such as a network. In another example, the control unit 34 may also be implemented by, for example, a DSP (Digital Signal Processor), an ASIC (Application-Specific Integrated Circuit), or an FPGA (Field-Programmable Gate Array). It should be understood that, for example, a GPU (Graphics Processing Unit) may also be used. The control unit 34 may be implemented by a single device, or the functions of the control unit 34 may be implemented by one or a plurality of devices.

Figure 4:
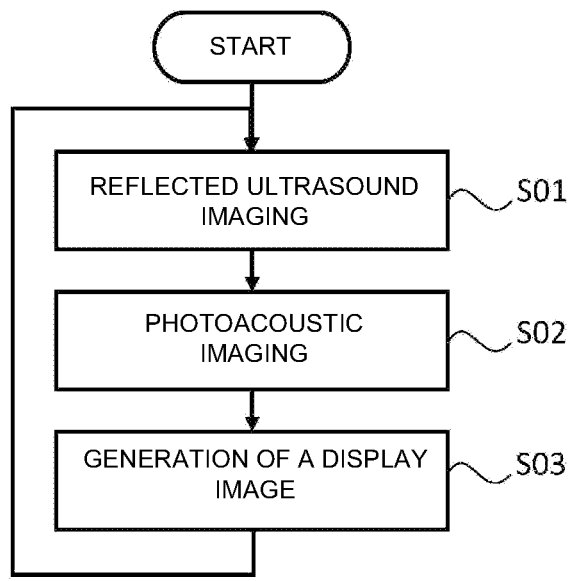
FIG. 4 is a flowchart illustrating an outline of the operation of the medical assistance system.

Referring to FIG. 4, an outline of the operation of the medical assistance system 10 will be described below. FIG. 4 is a flowchart illustrating an outline of the operation of the medical assistance system 10. By way of example here, the ultrasound imaging apparatus 12 performs the reflected ultrasound imaging using the ultrasound probe 18 that includes a 1D array transducer. The operator inserts into the subject the living body inserter 16 with the ultrasound generation source 22 incorporated therein. The driver 24 applies a laser beam to the ultrasound generation source 22 via the optical fiber in accordance with instructions from the control unit 34. As a result, photoacoustic waves are generated from the ultrasound generation source 22, and the ultrasound imaging apparatus 12 performs the photoacoustic imaging. The reflected ultrasound imaging and the photoacoustic imaging are performed in this manner, and a reflected ultrasound image and a photoacoustic image are displayed on the display unit 38. The living body inserter 16 and the ultrasound probe 18 are manually operated by, for example, the operator.

As illustrated in FIG. 4, the ultrasound imaging apparatus 12 repeats reflected ultrasound imaging (S01), photoacoustic imaging (S02), and generation of a display image (S03) with a predetermined cycle. It should be noted that the manner (such as the order) in which this repetition is performed is not limited to the manner illustrated in FIG. 4. For example, the ultrasound imaging apparatus 12 may repeat an operation in which the reflected ultrasound imaging is executed four times and then the photoacoustic imaging is executed once to generate a display image, or may repeat an operation in which the reflected ultrasound imaging and the photoacoustic imaging are each executed once and the generation of a display image is performed in parallel with each of the reflected ultrasound imaging and the photoacoustic imaging.

During the reflected ultrasound imaging (S01), the transmission unit 30 transmits ultrasound waves from the ultrasound probe 18 toward inside of the subject 26, and the ultrasound probe 18 receives reflected waves that are reflected by tissue inside the subject 26. The reception unit 32 applies phase alignment or other processing to reception signals and outputs, to the reflected ultrasound signal processing unit 48, the signals to which this processing has been applied. Based on the signals output from the reception unit 32, the reflected ultrasound signal processing unit 48 generates a reflected ultrasound image, such as a B-mode image. The reflected image filtering unit 50 applies filtering processing to the reflected ultrasound image and outputs, to the display image generation unit 46, the reflected ultrasound image to which the filtering processing has been applied. The reflected ultrasound signal processing unit 48 may generate a two-dimensional reflected ultrasound image that represents a scanning plane over which an ultrasound beam is scanned, or may generate a three-dimensional reflected ultrasound image (volume data).

During the photoacoustic imaging (S02), the imaging is performed with the living body inserter 16 being inserted inside the subject 26 (for example, inside the blood vessel 28). Specifically, the imaging control unit 44 briefly suspends transmission of ultrasound waves performed by the transmission unit 30 to emit a pulsed laser beam from the driver 24 (in other words, intermittently emit a laser beam from the driver 24). The laser beam emitted from the driver 24 is applied to the ultrasound generation source 22 via the optical fiber provided along the living body inserter 16. As a result, photoacoustic waves serving as ultrasound waves are generated from the ultrasound generation source 22, and the generated photoacoustic waves are received by the ultrasound probe 18. The reception unit 32 receives a photoacoustic signal received by the ultrasound probe 18 in synchronization with the emission of the laser beam from the driver 24 and applies phase alignment or other processing to the photoacoustic signal, and the photoacoustic signal to which this processing has been applied is output to the photoacoustic image processing unit 52. The photoacoustic image processing unit 52 images the photoacoustic signal, thereby generating a photoacoustic image. The photoacoustic image filtering unit 54 applies filtering processing to this photoacoustic image, and the photoacoustic image to which the filtering processing has been applied is output to the display image generation unit 46. It should be noted that the reception unit 32 may recognize emission timing of the laser beam based on a trigger signal output to the photoacoustic image processing unit 52 when the driver 24 has emitted the laser beam, or may estimate emission timing of the laser beam based on the photoacoustic waves received by the ultrasound probe 18.

Figure 5:
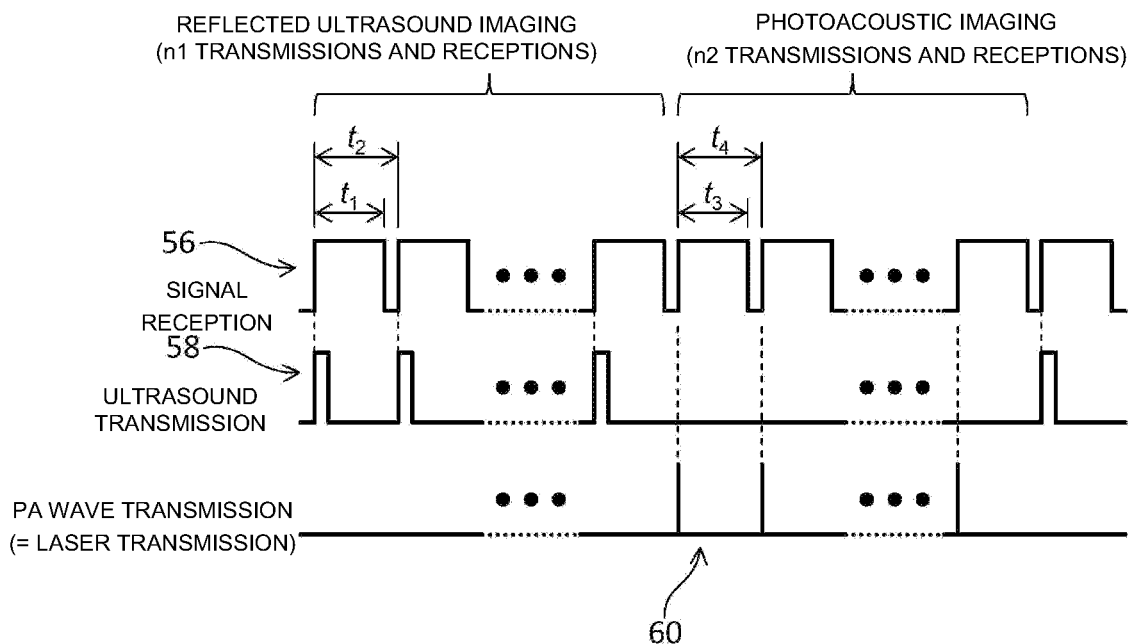
FIG. 5 is a sequence diagram illustrating timing of imaging according to a background art example.

Timing for each of the reflected ultrasound imaging and the photoacoustic imaging will be described below. FIG. 5 illustrates timing according to a background art example. The background art example is an example in which the operation according to an embodiment of the present disclosure is not used. The horizontal axis in FIG. 5 represents time t.

Referring to FIG. 5, reference numeral 56 represents timing of ultrasound reception performed by the reception unit 32. Reference numeral 58 represents timing of ultrasound transmission performed by the transmission unit 30. Reference numeral 60 represents timing of laser beam emission performed by the driver 24.

In the example illustrated in FIG. 5, the reflected ultrasound imaging is repeated $n_1$ times with an imaging cycle of every $t_2$ seconds, and the photoacoustic imaging is repeated $n_2$ times with an imaging cycle of every $t_4$ seconds. An imaging cycle for generating one ultrasound image is represented by the following formula (1):

$$n_1 \times t_2 + n_2 \times t_4 \tag{1}$$

The reflected ultrasound imaging is composed of ultrasound transmission performed by the transmission unit 30 and the ultrasound probe 18, and ultrasound reception synchronized with this ultrasound transmission (ultrasound reception performed by the reception unit 32 and the ultrasound probe 18) in a reception period of $t_1$ seconds. The reception period of $t_1$ seconds is typically determined in accordance with the depth of the target to be imaged (in other words, the depth of the imaging region); in other words, it is determined depending on the distance between the body surface of the subject 26 and the target to be imaged (more accurately, the distance between each of the ultrasound transducers of the ultrasound probe 18 and the target to be imaged). Assuming that, for example, the depth of a region of interest (in other words, the target to be imaged) is d [mm], in consideration of the time taken for an acoustic wave having a velocity of sound c [mm/s] to make a round trip between the ultrasound probe 18 and the target to be imaged, the reception period $t_1$ is determined in accordance with a condition represented by the following formula (2):

$$t_1 > 2 \times d/c \tag{2}$$

The imaging cycle $t_2$ should be longer than the reception period $t_1$ and therefore is determined in accordance with a condition represented by the following formula (3):

$$t_2 < t_1 \tag{3}$$

During the photoacoustic imaging, on the other hand, in consideration of the time taken for an acoustic wave having a velocity of sound c [mm/s] to propagate from the ultrasound generation source 22 to the ultrasound probe 18, the reception period $t_3$ is determined in accordance with a condition represented by the following formula (4):

$$t_3 > d/c \tag{4}$$

The imaging cycle $t_4$ should be longer than the reception period $t_3$ and therefore is determined in accordance with a condition represented by the following formula (5):

$$t_4 > t_3 \tag{5}$$

The imaging counts $n_1$ and $n_2$ are determined depending on the required image fidelity and SN (Signal to Noise) ratio. Assuming a constant image fidelity, the higher the imaging count, the greater number of reception signals can be used in subsequent processing such as averaging, and therefore an image having a higher SN ratio is obtained. As such, an imaged result having a higher SN ratio is obtained by increasing the imaging count $n_1$ or $n_2$. However, this causes an issue in that, as the imaging cycle for generating one ultrasound image is increased, the update cycle of the resulting ultrasound image will be longer. In other words, the ultrasound imaging frame rate decreases.

Figure 6:
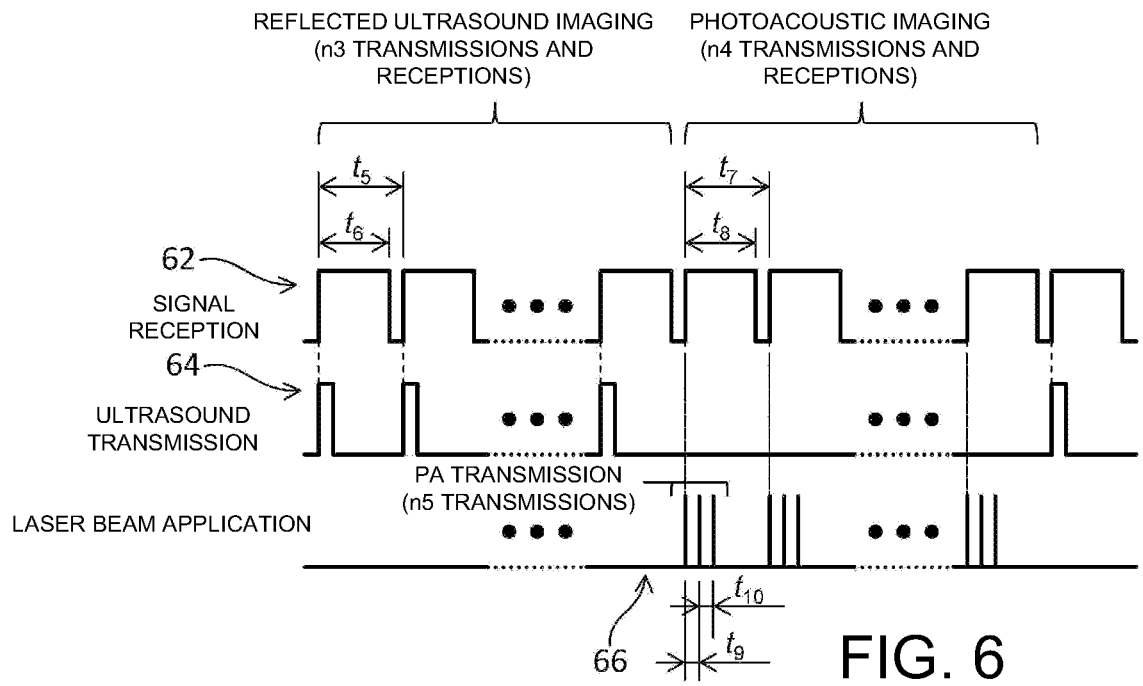
FIG. 6 is a sequence diagram illustrating timing of imaging according to an embodiment of the present disclosure.

Referring to FIG. 6, an operation according to an embodiment of the present disclosure will be described below. FIG. 6 illustrates timing according to an embodiment of the present disclosure. The timing according to the embodiment is timing with which a problem found in the background art example can be solved. The horizontal axis in FIG. 6 represents time.

Referring to FIG. 6, reference numeral 62 represents timing of ultrasound reception performed by the reception unit 32. Reference numeral 64 represents timing of ultrasound transmission performed by the transmission unit 30. Reference numeral 66 represents timing of laser beam emission performed by the driver 24.

In the example illustrated in FIG. 6, the reflected ultrasound imaging is repeated $n_3$ times with an imaging cycle of every $t_5$ seconds, and the photoacoustic imaging is repeated $n_4$ times with an imaging cycle of every $t_7$ seconds. An imaging cycle for generating one ultrasound image is represented by the following formula (6):

$$n_3 \times t_5 + n_4 \times t_7 \qquad (6)$$

Timing of the reflected ultrasound imaging is equivalent to timing of the reflected ultrasound imaging according to the background art example (see FIG. 5). Specifically, the reflected ultrasound imaging is composed of ultrasound transmission performed by the transmission unit 30 and the ultrasound probe 18, and ultrasound reception synchronized with this ultrasound transmission (ultrasound reception performed by the reception unit 32 and the ultrasound probe 18) in a reception period of $t_6$ seconds. The reception period of $t_6$ seconds is, as described above, determined in accordance with the depth of the target to be imaged. For reasons similar to those described above for the formula (2), the reception period $t_6$ is determined in accordance with a condition represented by the following formula (7):

$$t_6 > 2 \times d/c \qquad (7)$$

The imaging cycle $t_5$ should be longer than the reception period $t_6$ and therefore is determined in accordance with a condition represented by the following formula (8):

$$t_5 > t_6 \qquad (8)$$

The reception period $t_8$ for the photoacoustic imaging is, as for the above-described formula (4), determined in accordance with a condition represented by the following formula (9):

$$t_8 > d/c \qquad (9)$$

The imaging cycle $t_7$ should be longer than the reception period $t_8$ and therefore is determined in accordance with a condition represented by the following formula (10):

$$t_7 > t_8 \qquad (10)$$

During the photoacoustic imaging according to the embodiment, the imaging control unit 44 causes the driver 24 to emit a laser beam multiple times in response to one instance of reception. In other words, the imaging control unit 44 causes the driver 24 to emit a laser beam multiple times during the reception period $t_8$. As a result, a laser beam is applied to the ultrasound generation source 22 multiple times during the reception period $t_8$, and a plurality of photoacoustic waves are generated from the ultrasound generation source 22 during the reception period $t_8$. A laser beam emission count per instance of reception is defined as count $n_5$ ($n_5 \geq 2$). As a laser beam is applied to the ultrasound generation source 22 multiple times in response to one instance of reception, the laser beam emission count is not limited by the reception period $t_8$ that is determined by the depth of the target to be imaged that is of interest (in other words, a region of interest).

In the example illustrated in FIG. 6, $n_5=3$; that is, the imaging control unit 44 causes the driver 24 to emit a laser beam three times during one instance of reception (in other words, during the reception period $t_8$). As a result, one reception signal includes three photoacoustic waves. The photoacoustic image processing unit 52 sums the three photoacoustic waves. The photoacoustic image processing unit 52 may sum three photoacoustic signals output from the reception unit 32 or may sum three photoacoustic wave images that are generated through the application of signal processing. This summation provides a high SN ratio.

In the example illustrated in FIG. 6, the imaging control unit 44 causes the driver 24 to emit a laser beam with the instant at which reception starts being synchronized with the instant at which the laser beam is emitted. Specifically, the imaging control unit 44 causes the driver 24 to emit a first laser beam at the same time as the instant at which reception starts (in other words, the instant at which the reception period $t_8$ starts). The imaging control unit 44 causes the driver 24 to emit a second laser beam period $t_9$ seconds later than the instant at which the first laser beam is emitted. The imaging control unit 44 causes the driver 24 to emit a third laser beam period $t_{10}$ seconds later than the instant at which the second laser beam is emitted. The period $t_9$ and the period $t_{10}$ may be the same length of time or may be different lengths of time. The periods $t_9$ and $t_{10}$ are periods of time shorter than the reception period $t_8$, and the sum of the period $t_9$ and the period $t_{10}$ is also a period of time shorter than the reception period $t_8$. For example, the periods $t_7$ and $t_8$ (similarly, the periods $t_5$ and $t_6$) are periods of time that are on the order of microseconds (µs), and the periods $t_9$ and $t_{10}$ are periods of time that are on the order of nanoseconds (ns).

Figure 7:
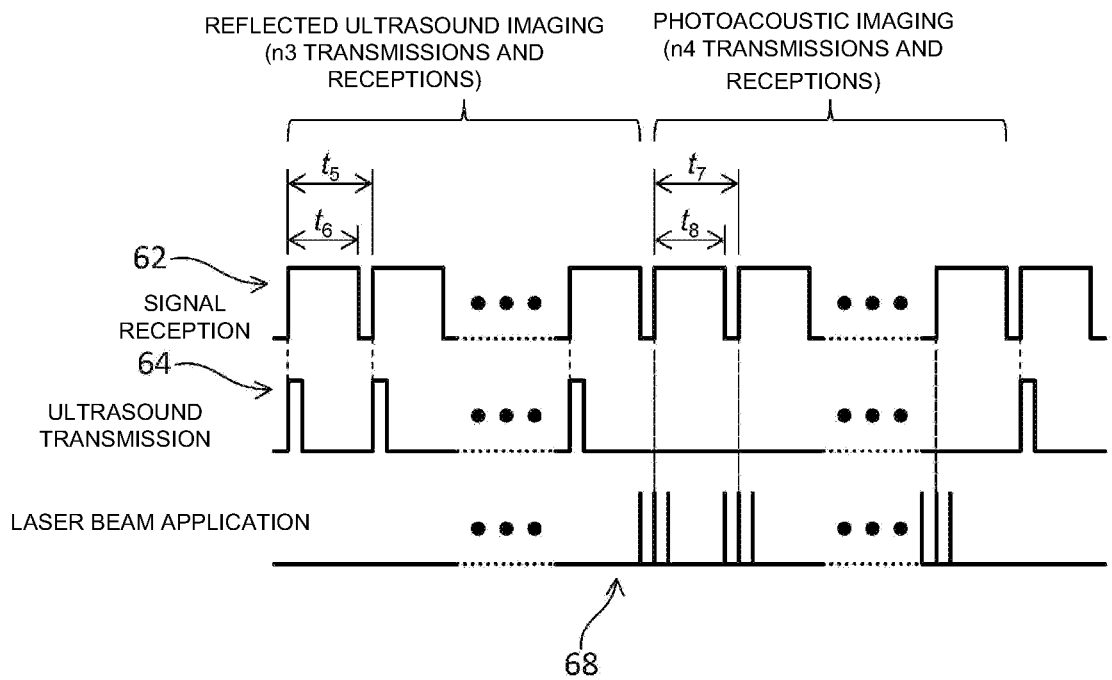
FIG. 7 is a sequence diagram illustrating timing of imaging according to an embodiment of the present disclosure.

FIG. 7 illustrates timing according to another example of the embodiment of the present disclosure. Referring to FIG. 7, reference numeral 68 represents timing of laser beam emission performed by the driver 24.

In the example illustrated in FIG. 7, the instant at which a laser beam is emitted is earlier than the instant at which reception starts. In other words, the imaging control unit 44 causes the driver 24 to emit a laser beam at an instant earlier than the instant at which reception starts. For example, the imaging control unit 44 causes the driver 24 to emit a first laser beam at an instant earlier than the instant at which reception starts (in other words, the instant at which the reception period $t_8$ starts), causes the driver 24 to emit a second laser beam at the same time as the instant at which reception starts, and subsequently causes the driver 24 to emit a third laser beam. The imaging control unit 44 controls the emission timing of the first laser beam so that a photoacoustic wave generated from the ultrasound generation source 22 in response to the emission of the first laser beam is received by the reception unit 32 within the reception period $t_8$. It should be noted that the difference between the instant at which reception starts and the instant at which each laser beam is emitted may be constant or may be a predetermined value that is not constant.

Figure 8:
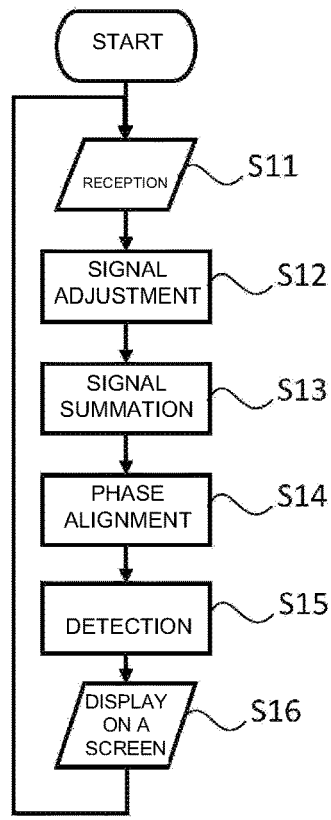
FIG. 8 is a flowchart illustrating a series of processing steps according to an embodiment of the present disclosure.

Referring to FIG. 8, an example of processing according to the embodiment of the present disclosure will be described below. FIG. 8 is a flowchart illustrating a series of processing steps according to the embodiment.

The reception unit 32 receives a photoacoustic wave each time photoacoustic imaging is performed (S11). In the example illustrated in FIG. 6, the reception unit 32 receives three photoacoustic waves every reception period $t_8$. The photoacoustic image processing unit 52 adjusts photoacoustic signals which are received by the reception unit 32 and to which phase alignment has not been applied (S12) and sums a plurality of photoacoustic signals which have been adjusted (S13). The photoacoustic image processing unit 52 then phase aligns the photoacoustic signals which have been summed (S14) and performs detection (S15). As a result, a photoacoustic image is generated and displayed on the display unit 38 (S16).

Figure 9:
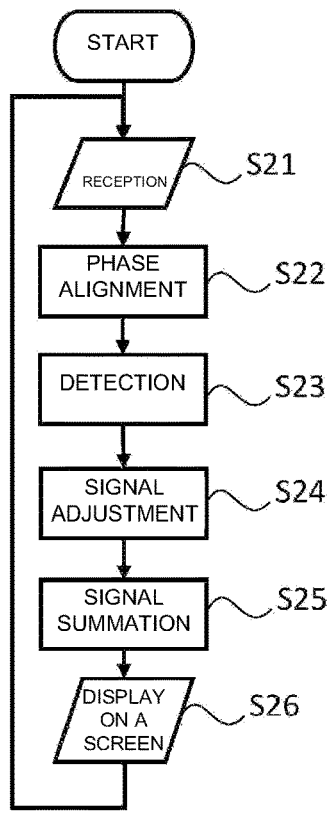
FIG. 9 is a flowchart illustrating a series of processing steps according to an embodiment of the present disclosure.

FIG. 9 illustrates another example of a processing method according to the embodiment.

The reception unit 32 receives a photoacoustic wave each time photoacoustic imaging is performed (S21). The photoacoustic image processing unit 52 phase aligns photoacoustic signals which are received by the reception unit 32 (S22) and performs detection (S23). The photoacoustic image processing unit 52 then adjusts photoacoustic signals which have been phase aligned (S24) and sums a plurality of photoacoustic signals which have been adjusted (S25). A generated photoacoustic image is displayed on the display unit 38 (S26).

Figure 10:
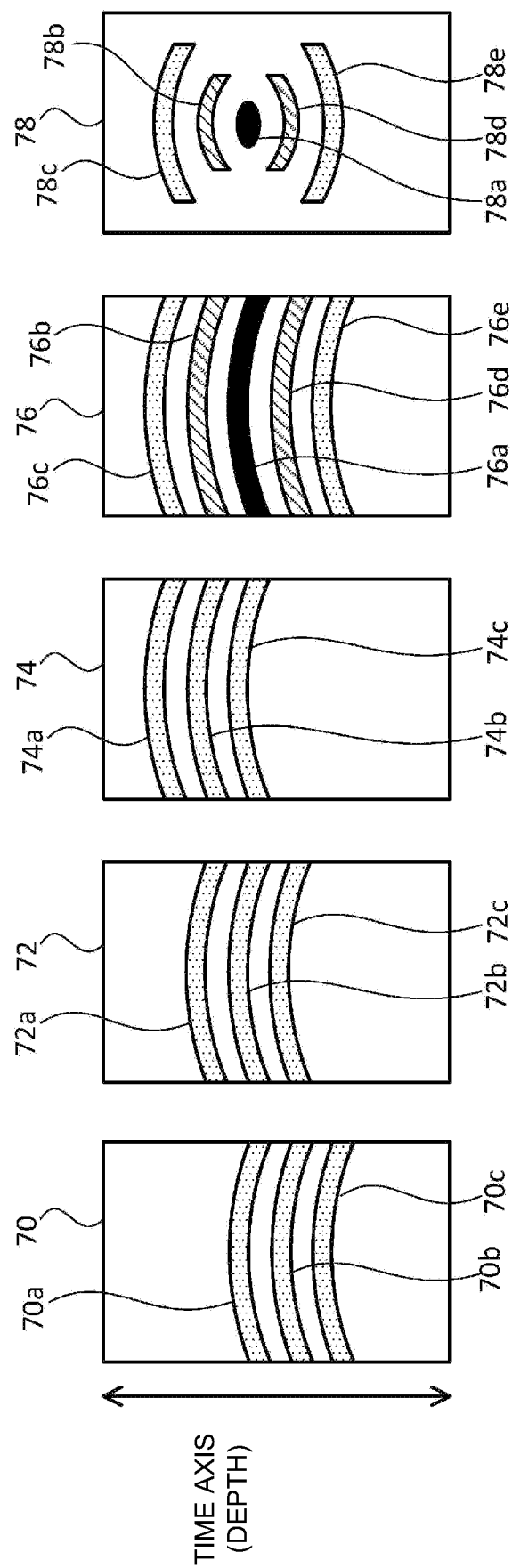
FIG. 10 illustrates reception signals and images obtained through photoacoustic imaging.

Referring to FIG. 10, a specific example of the above-described adjustment method (S12 and S24) will be described below. FIG. 10 illustrates reception signals and images obtained through photoacoustic imaging. FIG. 10 illustrates a time axis that corresponds to depth as measured from the body surface of the subject 26. By way of example here, a laser beam is applied to the ultrasound generation source 22 three times during one instance of reception (in other words, within the reception period $t_8$), as illustrated in FIG. 6 or FIG. 7.

A reception signal 70 is a signal that is received by the reception unit 32 within the reception period $t_8$ in response to performing the photoacoustic imaging. The reception signal 70 is a signal to which phase alignment has not been applied. The reception signal 70 includes three photoacoustic signals that are received in response to one instance of reception. In other words, during one instance of reception (in other words, within the reception period $t_8$), a laser beam is applied to the ultrasound generation source 22 three times, and a photoacoustic wave is generated from the ultrasound generation source 22 three times. As such, the reception signal 70 includes three photoacoustic signals that are received within the reception period $t_8$. For example, the reception signal 70 includes photoacoustic signals 70b, and 70c. The photoacoustic signal 70a is a photoacoustic signal that is received in response to the first laser beam emission of the three emissions. The photoacoustic signal is a photoacoustic signal that is received in response to the second laser beam emission of the three emissions. The photoacoustic signal 70c is a photoacoustic signal that is received in response to the third laser beam emission of the three emissions. A time interval between the photoacoustic signal 70a and the photoacoustic signal 70b (time interval on the time axis) corresponds to the period $t_9$ illustrated in FIG. 6. A time interval between the photoacoustic signal 70b and the photoacoustic signal 70c (time interval on the time axis) corresponds to the period $t_{10}$ illustrated in FIG. 6. By way of example here, the period $t_9$ and the period $t_{10}$ are the same.

As such, the time interval between the photoacoustic signal 70a and the photoacoustic signal 70b (time interval on the time axis) and the time interval between the photoacoustic signal 70b and the photoacoustic signal 70c (time interval on the time axis) are the same. It should be understood that the period $t_9$ and the period $t_{10}$ may be different. In this case, the time interval between the photoacoustic signal 70a and the photoacoustic signal 70b (time interval on the time axis) and the time interval between the photoacoustic signal 70b and the photoacoustic signal 70c (time interval on the time axis) are different.

A reception signal 72 is a signal that is generated by shifting the position of the reception signal 70 on the time axis in a temporal direction with reference to the position of the second photoacoustic signal 70b on the time axis. The reception signal 72 is a signal to which phase alignment has not been applied. For example, the photoacoustic image processing unit 52 corrects transmission delay of the reception signal 70, thereby shifting the position of the reception signal 70 on the time axis in the temporal direction with reference to the position of the photoacoustic signal 70b on the time axis. As a result, the reception signal 72 is generated. Specifically, the photoacoustic image processing unit 52 shifts the position of the reception signal 70 on the time axis by the period $t_9$ in the temporal direction, thereby generating the reception signal 72. As a result, the positions of the photoacoustic signals 70a, 70b, and 70c included in the reception signal 70 on the time axis shift by the period $t_9$ in the temporal direction. The reception signal 72 includes photoacoustic signals 72a, 72b, and 72c. The photoacoustic signal 72a is a signal that is generated by shifting the position of the photoacoustic signal 70a on the time axis by the period $t_9$ in the temporal direction. The photoacoustic signal 72b is a signal that is generated by shifting the position of the photoacoustic signal 70b on the time axis by the period $t_9$ in the temporal direction. The photoacoustic signal 72c is a signal that is generated by shifting the position of the photoacoustic signal 70c on the time axis by the period $t_9$ in the temporal direction. The time interval between the photoacoustic signal 70a and the photoacoustic signal 70b corresponds to the period $t_9$. As such, shifting the position of the reception signal on the time axis by the period $t_9$ in a direction such that the second photoacoustic signal 70b coincides with the first photoacoustic signal 70a causes the photoacoustic signal 72b, which has been shifted, to be located at the same position as the photoacoustic signal 70a, which has not been shifted. This enables summation of the photoacoustic signal 72b and the photoacoustic signal 70a that are located at the same position, as will be described later.

A reception signal 74 is a signal that is generated by shifting the position of the reception signal 70 on the time axis in the temporal direction with reference to the position of the third photoacoustic signal 70c on the time axis. The reception signal 74 is a signal to which phase alignment has not been applied. For example, the photoacoustic image processing unit 52 corrects transmission delay of the reception signal 70, thereby shifting the position of the reception signal 70 on the time axis in the temporal direction with reference to the position of the photoacoustic signal 70c on the time axis. As a result, the reception signal 74 is generated. Specifically, the photoacoustic image processing unit 52 shifts the position of the reception signal 70 on the time axis by the sum of the period $t_9$ and the period $t_{10}$ in the temporal direction, thereby generating the reception signal 74. As a result, the positions of the photoacoustic signals 70a, 70b, and 70c included in the reception signal 70 on the time axis shift by the sum of the period $t_9$ and the period $t_{10}$ in the temporal direction. In other words, the photoacoustic image processing unit 52 shifts the position of the reception signal 72 on the time axis by the period $t_{10}$ in the temporal direction, thereby generating the reception signal 74. The reception signal 74 includes photoacoustic signals 74a, 74b, 74c. The photoacoustic signal 74a is a signal that is generated by shifting the position of the photoacoustic signal 70a on the time axis by the sum of the period $t_9$ and the period $t_{10}$ in the temporal direction. The photoacoustic signal 74b is a signal that is generated by shifting the position of the photoacoustic signal 70b on the time axis by the sum of the period $t_9$ and the period $t_{10}$ in the temporal direction. The photoacoustic signal 74c is a signal that is generated by shifting the position of the photoacoustic signal 70c on the time axis by the sum of the period $t_9$ and the period $t_{10}$ in the temporal direction. A time interval between the photoacoustic signal 70a and the photoacoustic signal 70c corresponds to the sum of the period $t_9$ and the period $t_{10}$. As such, shifting the position of the reception signal 70 on the time axis by the sum of the period $t_9$ and the period $t_{10}$ in a direction such that the third photoacoustic signal 70c coincides with the first photoacoustic signal 70a causes the photoacoustic signal 74c, which has been shifted, to be located at the same position as the photoacoustic signal 70a, which has not been shifted. This enables summation of the photoacoustic signal 74c and the photoacoustic signal 70a that are located at the same position, as will be described later. Additionally, as the position of the photoacoustic signal 72b is also the same as the positions of the photoacoustic signal 74c and the photoacoustic signal 70a, summation of the photoacoustic signal 70a, the photoacoustic signal 72b, and the photoacoustic signal 74c is performed.

A reception signal 76 is a signal that is generated by averaging the reception signals 70, 72, and 74. The reception signal 76 is a signal to which phase alignment has not been applied. For example, the photoacoustic image processing unit 52 averages the reception signals 70, 72, and 74, thereby generating the reception signal 76. The reception signal 76 includes photoacoustic signals 76a to 76e obtained as the results of averaging. The photoacoustic signal 76a is a signal that is generated by averaging the photoacoustic signals 70a, 72b, and 74c that are located at the same position. The photoacoustic signal 76b is a signal that is generated by averaging the photoacoustic signals 72a and 74b that are located at the same position. The photoacoustic signal 76c is the same signal as the photoacoustic signal 74a. The photoacoustic signal 76d is a signal that is generated by averaging the photoacoustic signals 70b and 72c that are located at the same position. The photoacoustic signal 76e is the same signal as the photoacoustic signal 70c.

A photoacoustic image 78 is an image that is generated by phase aligning and imaging the reception signal 76. The phase alignment and imaging processing are performed by the photoacoustic image processing unit 52. The photoacoustic image 78 includes images 78a to 78e. The image 78a is an image that is generated based on the photoacoustic signal 76a of the reception signal 76. The image 78b is an image that is generated based on the photoacoustic signal 76b. The image 78c is an image that is generated based on the photoacoustic signal 76c. The image 78d is an image that is generated based on the photoacoustic signal 76d. The image 78e is an image that is generated based on the photoacoustic signal 76e.

As described above, three photoacoustic signals are averaged with the positions of the three photoacoustic signals on the time axis being aligned, thereby generating the image 78a. The image 78a with an improved SN ratio is generated by averaging a plurality of photoacoustic signals in this manner. The image 78a is an image that represents the ultrasound generation source 22. As the operator or some other user can see the image 78a with an improved SN ratio, it is easy for the operator or some other user to recognize the tip position of the living body inserter 16.

Besides the image 78a that represents the ultrasound generation source 22, the photoacoustic image 78 includes the images 78b to 78e. The images 78b to 78e are artifacts that appear at positions where the ultrasound generation source 22 is absent.

Figure 11:
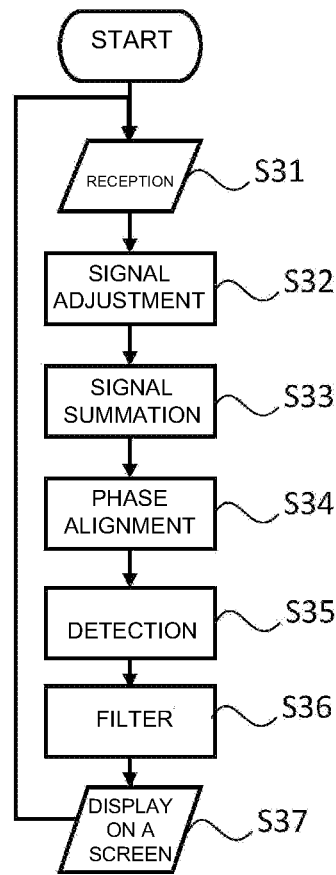
FIG. 11 is a flowchart illustrating a series of processing steps including filtering.

FIG. 11 illustrates an example of processing including the removal of such artifacts. Steps S31 to S35 in FIG. 11 are the same as steps S11 to S15 in FIG. 8. Also, step S37 in FIG. 11 is the same as step S16 in FIG. 8. In the example illustrated in FIG. 11, before image display, the photoacoustic image filtering unit 54 removes the images 78b to 78e included in the photoacoustic image 78 (S36). The photoacoustic image 78 from which the images 78b to 78e have been removed is displayed on the display unit 38 (S37).

Examples of the artifact removal filter include a filter that removes images other than the highest brightness image (for example, the image 78a), an image statistical information-based filter, or a machine learning-based filter. It should be understood that filters other than these may be used.

The photoacoustic image filtering unit 54 may apply filtering processing to a photoacoustic signal for which summation processing has not been performed, or may apply filtering processing to a photoacoustic signal or a photoacoustic image for which summation processing has been performed. The application of filtering processing to a signal having an SN ratio that is improved through summation processing is more advantageous in terms of accuracy or stability than the application of filtering processing before summation processing.

It should be noted that, without the application of filtering to the photoacoustic image 78, the display unit 38 may display the photoacoustic image 78 including the images 78b to 78e that are artifacts. In this case as well, the operator or some other user can monitor the approximate position of the ultrasound generation source 22 (in other words, the tip of the living body inserter 16).

A modification example will be described below.

In consideration of, for example, various regulations or durability of dye in the ultrasound generation source 22 for generating photoacoustic waves, the power (for example, average power) of the laser beam emitted from the driver 24 may be a predetermined limit value or less. The limit value is determined based on, for example, various regulations or durability of dye. However, the higher the intensity of the laser beam, the greater the improvement in the SN ratio of the photoacoustic signal. In consideration of this, the imaging control unit 44 may change the intensity of the laser beam or the light emission period per instance of light emission so that the power (for example, average power) of the laser beam is the limit value or less, and so that the difference between the power of the laser beam and an upper limit value is a threshold value or less. For example, the imaging control unit 44 may change the intensity of the laser beam or the light emission period per instance of light emission depending on the laser beam emission count or the interval between light emissions. Specifically, the emission count during one instance of reception is around two to five times, but it should be understood that the emission count may be six times or a greater number of times, so long as the power of the laser beam is the limit value or less.

Figure 12:
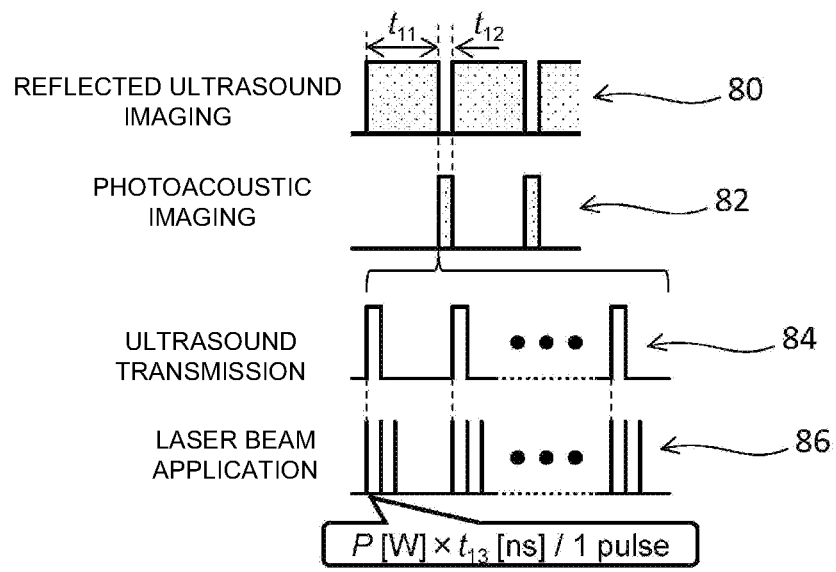
FIG. 12 is a sequence diagram illustrating timing of imaging according to a modification example.
Figure 13:
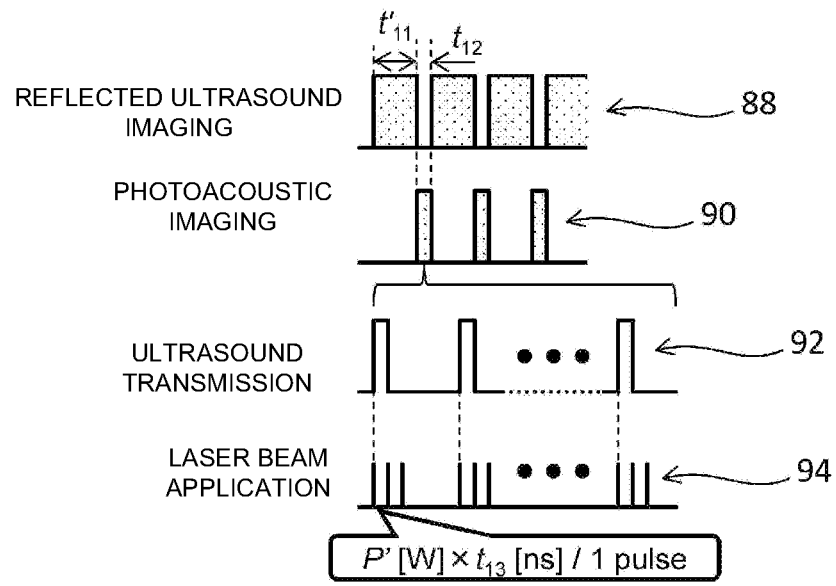
FIG. 13 is a sequence diagram illustrating timing of imaging according to a modification example.

Referring to FIGS. 12 and 13, processing according to a modification example will be described in detail below. FIGS. 12 and 13 illustrate reflected ultrasound imaging and photoacoustic imaging sequences according to a modification example. The horizontal axis in FIGS. 12 and 13 represents time.

Referring to FIG. 12, reference numeral 80 represents timing of reflected ultrasound imaging. Reference numeral 82 represents timing of photoacoustic imaging. Reference numeral 84 represents timing of ultrasound transmission performed by the transmission unit 30. Reference numeral 86 represents timing of laser beam emission performed by the driver 24.

Referring to FIG. 13, reference numeral 88 represents timing of reflected ultrasound imaging. Reference numeral 90 represents timing of photoacoustic imaging. Reference numeral 92 represents timing of ultrasound transmission performed by the transmission unit 30. Reference numeral 94 represents timing of laser beam emission performed by the driver 24.

In the example illustrated in FIG. 12, the duration period to perform reflected ultrasound imaging is $t_{11}$, and in the example illustrated in FIG. 13, the duration period to perform reflected ultrasound imaging is $t'_{11}$. By way of example here, $t_{11} > t'_{11}$. The duration period is changed due to, for example, image adjustment. For example, a longer duration period results in generation of a more detailed reflected ultrasound image. Image adjustment or other processing is, for example, set by the operator or some other user. For example, the imaging control unit 44 sets a duration period having a length that corresponds to a set value for image adjustment. The operator may set a duration period directly. It should be understood that the duration period may be changed for some other reason.

In both examples illustrated in FIGS. 12 and 13, the duration period to perform photoacoustic imaging is $t_{12}$, and the reflected ultrasound imaging and the photoacoustic imaging are alternately executed repeatedly. In other words, in the example illustrated in FIG. 12, the reflected ultrasound imaging is executed for the duration period $t_{11}$, then the photoacoustic imaging is executed for the duration period $t_{12}$, and from then on, the reflected ultrasound imaging and the photoacoustic imaging are alternately executed repeatedly. In the example illustrated in FIG. 13, the reflected ultrasound imaging is executed for the duration period $t'_{11}$, then the photoacoustic imaging is executed for the duration period $t_{12}$, and from then on, the reflected ultrasound imaging and the photoacoustic imaging are alternately executed repeatedly.

In the example illustrated in FIG. 12, the light emission intensity of the laser beam per instance of light emission is light emission intensity P [W], and the light emission period of the laser beam per instance of light emission is light emission period $t_{13}$ [ns].

In the example illustrated in FIG. 13, the light emission intensity of the laser beam per instance of light emission is light emission intensity P'[W], and the light emission period of the laser beam per instance of light emission is light emission period $t_{13}$ [ns].

The difference in light emission intensity is attributable to the difference in the duration period to perform reflected ultrasound imaging. The light emission intensity P is determined based on the periods $t_{11}$, $t_{12}$, and $t_{13}$ and the limit value $P_{limit}$ [W] for the average power of the laser beam. Similarly, the light emission intensity P' is determined based on the periods $t'_{11}$, $t_{12}$, and $t_{13}$ and the limit value $P_{limit}$ [W] for the average power of the laser beam. Specifically, the light emission intensities P and P' are determined in accordance with the following formula (11):

$$P_{limit} \simeq \frac{P \times t_{13}}{t_{11} + t_{12}} \simeq \frac{P' \times t_{13}}{t'_{11} + t_{12}} \quad (11)$$

In the example above, the imaging control unit 44 changes the light emission intensity of the laser beam depending on the duration period to perform reflected ultrasound imaging. The method of changing the light emission intensity or the light emission period of the laser beam is not limited to the above-described example. For example, the imaging control unit 44 may change the light emission intensity or the light emission period of the laser beam depending on another parameter such as the imaging period or the imaging count.

Figure 14:
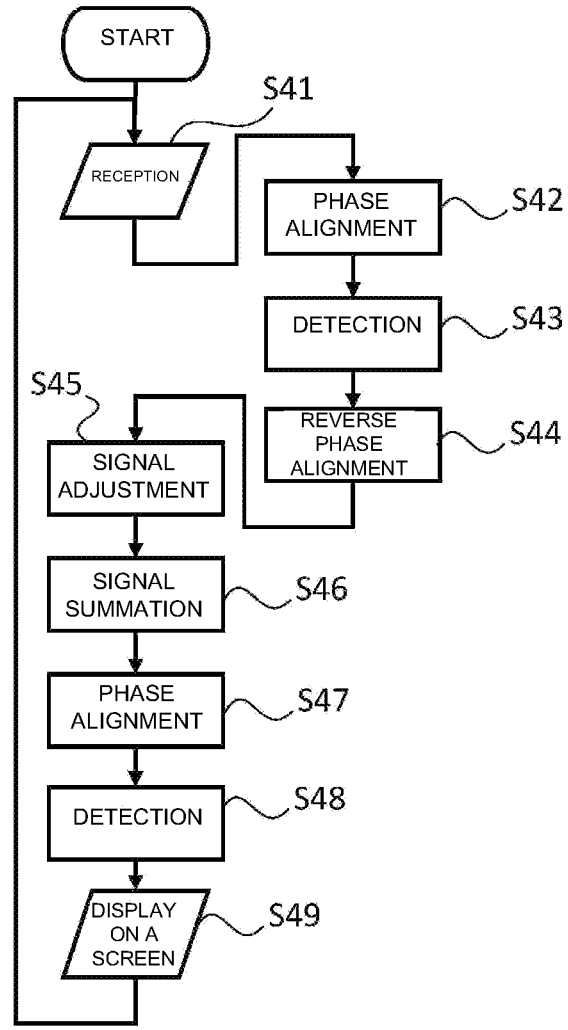
FIG. 14 is a flowchart illustrating a series of steps performed in a signal processing method according to a modification example.

Referring to FIG. 14, a modification example of a signal processing method will be described below. FIG. 14 is a flowchart illustrating a series of steps performed in a signal processing method according to the modification example.

The reception unit 32 receives a photoacoustic wave each time photoacoustic imaging is performed (S41). The photoacoustic image processing unit 52 phase aligns photoacoustic signals which are received by the reception unit 32 (S42) and performs detection (S43). The photoacoustic image processing unit 52 then estimates a signal to which phase alignment has not been applied, through reverse phase alignment processing from a signal for which detection has been performed (S44). The photoacoustic image processing unit 52 then adjusts estimated signals to which phase alignment has not been applied (S45) and sums a plurality of signals which have been adjusted (S46). The photoacoustic image processing unit 52 then phase aligns signals which have been summed (S47) and performs detection (S48). As a result, a photoacoustic image is generated and displayed on the display unit 38 (S49). The reverse phase alignment processing can be implemented using machine learning-based or Fourier phase alignment-based processing. The reverse phase alignment processing may be applied to the entire signal, or the reverse phase alignment processing may be applied to some signals that include a photoacoustic signal.

The processing according to an embodiment of the present disclosure is not limited to the above-described processing. Various embodiments of the present disclosure including the processing of changing the positions of a plurality of photoacoustic signals included in a reception signal on the time axis followed by summation of the plurality of photoacoustic signals are contemplated.

The invention claimed is:

1. An ultrasound imaging apparatus comprising a processor and a program storage device tangibly embodying a program of instructions executable by the processor, the ultrasound imaging apparatus including the processor performing a method comprising:

controlling transmission and reception of ultrasound waves toward and from a subject, to generate an ultrasound image; and repeating, in cycles, generation of photoacoustic waves from a photoacoustic wave generation source inserted within the subject and receiving the photoacoustic waves, thereby imaging a position of the photoacoustic wave generation source, the photoacoustic waves from the photoacoustic wave generation source being generated with a time interval shorter than a reception period during which the photoacoustic waves generated from the photoacoustic wave generation source are received, the reception period being determined based on a region that is to be imaged using photoacoustic waves, and the photoacoustic waves from the photoacoustic wave generation source being generated a number of times in the reception period of one cycle, said number of times corresponding to a plurality of times.

2. The ultrasound imaging apparatus according to claim 1, wherein the number of times for generating the photoacoustic waves in the reception period of one cycle is determined based on a limit value for an intensity of light applied to the photoacoustic wave generation source for generating photoacoustic waves from the photoacoustic wave generation source.

3. The ultrasound imaging apparatus according to claim 1, wherein the in the method, the processor changes an intensity and a light emission period of light applied to the photoacoustic wave generation source for generating photoacoustic waves from the photoacoustic wave generation source depending on a count of light emissions of the light applied to the photoacoustic wave generation source for generating photoacoustic waves from the photoacoustic wave generation source and an interval between the light emissions.

4. The ultrasound imaging apparatus according to claim 1, wherein in the method, the position of the photoacoustic wave generation source is imaged based on a plurality of photoacoustic waves received in the reception period.

5. The ultrasound imaging apparatus according to claim 4, wherein in the method, the processor further removes an artifact that occurs in response to the plurality of photoacoustic waves.

6. The ultrasound imaging apparatus according to claim 4, wherein in the method, the processor applies phase alignment processing to the plurality of photoacoustic waves and averages the plurality of photoacoustic waves to which phase alignment has been applied, with the positions of the plurality of photoacoustic waves on a time axis being adjusted.

7. The ultrasound imaging apparatus according to claim 4, wherein in the method, the processor averages the plurality of photoacoustic waves to which phase alignment has not been applied, with the positions of the plurality of photoacoustic waves on a time axis being adjusted.

8. The ultrasound imaging apparatus according to claim 7, wherein in the method, the processor estimates a photoacoustic wave to which phase alignment processing has not been applied, through reverse phase alignment processing from a result obtained after phase alignment processing has been applied.

* * * * *